(12) United States Patent
Brown

(10) Patent No.: US 6,425,862 B1
(45) Date of Patent: Jul. 30, 2002

(54) INTERACTIVE FURNITURE FOR DIETERS

(76) Inventor: Norma Brown, 2721 Kings Hwy., Apt. 4M, Brooklyn, NY (US) 11229

( * ) Notice: Subject to any disclaimer, the term of this patent is extended or adjusted under 35 U.S.C. 154(b) by 0 days.

(21) Appl. No.: 09/799,458

(22) Filed: Mar. 5, 2001

(51) Int. Cl.[7] .................. A61B 5/00; A61B 5/117; G06F 17/00; G06F 1/16; G09B 19/00; A47B 91/00; A47B 85/00; G01G 23/18; A47C 31/00

(52) U.S. Cl. .............. 600/300; 600/301; 600/590; 128/904; 128/921; 434/127; 312/351.4; 361/683; 361/724; 708/132; 177/25.19; 108/25; D06/396; 297/217.2; 297/115

(58) Field of Search ............... 600/300–301, 600/481–486, 500–503, 529, 532, 538, 587, 590, 595, 547; 128/903, 904, 920–925, 897–898; 482/142, 900–902; 434/127, 236, 238, 262, 270; 372/351.4; 361/683, 724; 108/50.11, 161, 25–26.2; 297/115–117, 135, 217.2, 217.1; 708/131–133; D06/396; 177/25.11–25.14, 25.16, 25.19; 705/2–4

(56) References Cited

U.S. PATENT DOCUMENTS

| | | | | |
|---|---|---|---|---|
| 5,067,488 A | * | 11/1991 | Fukada et al. | 600/590 |
| 5,233,520 A | * | 8/1993 | Kretsch et al. | 128/921 |
| 5,388,043 A | * | 2/1995 | Hettinger | 128/921 |
| 5,410,471 A | * | 4/1995 | Alyfuku et al. | 600/301 |
| 5,544,649 A | * | 8/1996 | David et al. | 600/300 |
| 5,680,820 A | * | 10/1997 | Randolph | 108/25 |
| 5,722,418 A | * | 3/1998 | Bro | 600/300 |
| 5,750,937 A | * | 5/1998 | Johnson et al. | 177/25.11 |
| 5,755,650 A | * | 5/1998 | Urso | 482/138 |
| 5,817,006 A | * | 10/1998 | Bergh et al. | 600/300 |
| 5,839,901 A | * | 11/1998 | Karkanen | 434/127 |
| 5,954,640 A | * | 9/1999 | Szabo | 600/300 |
| 5,961,446 A | * | 10/1999 | Beller et al. | 600/300 |
| 6,010,452 A | * | 1/2000 | Harcourt | 600/300 |
| 6,039,688 A | * | 3/2000 | Douglas et al. | 600/300 |
| 6,050,940 A | * | 4/2000 | Braun et al. | 600/300 |
| 6,169,655 B1 | * | 1/2001 | Helot | 361/686 |
| 6,206,829 B1 | * | 3/2001 | Iliff | 600/300 |
| 6,270,466 B1 | * | 8/2001 | Weinstein et al. | 600/590 |
| 6,336,136 B1 | * | 1/2002 | Harris | 709/219 |

* cited by examiner

*Primary Examiner*—Kevin Shaver
*Assistant Examiner*—Michael Astorino
(74) *Attorney, Agent, or Firm*—Michael I Kroll

(57) ABSTRACT

The present invention 10 discloses a horseshoe-shaped table 12 having a computer 14 and a dual-purpose chair 16 associated therewith. The chair 16 adjusts to variously sized users 11 by using a piston 78 and piston support mechanism disposed internally of the chair. The chair also serves as a weight scale or sensor 18 which is disposed in the seat thereof and has data input means, including a headset 27 with microphone 28 and chewing sensor 24 disposed thereon. The arm 36 of the chair has a blood pressure sensor 26 disposed thereon. Data gathered from the sensor input devices is transmitted to a computer 14 disposed internally of the table 12 having a monitor 40 and keypad 42 disposed on the tabletop. Also shown are a pair of scales 20, 22 which measure both the individual meal food and the daily food allowance which data is also input into the computer 14. The scales are equipped with segmented platters 90 and non-segmented platters 104, having various food compartments for receiving different types of food. The monitor 42 is disposed on a suspension arm 58 which is adjustable and is provided with a control crank 60 for adjusting the arm 58. The data inputs 48, 52 are disposed near the computer in order to receive input data from the input devices. An alternative embodiment of the present invention is disclosed wherein data is transmitted from the chair 16 via electromagnetic means 111, 116 to the table 12 wherein the chair is electrically operated and the monitor 40, and food scales 20, 22 are mounted internal of the table 12 being covered by panels 112 in the closed position and having a control panel 114 for electrically raising these elements from internal of the tables.

12 Claims, 14 Drawing Sheets

INTERACTIVE FURNITURE FOR DIETERS

BACKGROUND OF THE INVENTION

1. Field of the Invention

The present invention relates generally to furniture and, more specifically to interactive furniture for dieters designed to enable an obese person to engage in a technologically induced environ which promotes behavior modification, socialization and knowledge. Obese people often have a multiplicity of problems ranging from physical and social isolation, a sedentary lifestyle and a lack of basic nutritional knowledge. Each problem exacerbates the condition of obesity thereby creating a cycle of despair, defeat, and an increasing sense of isolation thus leading to increased eating and inertia. The present invention seeks to provide technological support through the use of a multi-media computer built into furniture designed exclusively for the modification of negative behaviors contributing to obesity. Additionally it seeks to create an environment conducive to healthy eating habits, exercise, increased self-esteem and a more rewarding lifestyle. The present invention coordinates sensory, dietary and exercise components into one integrated unit thereby associating eating, exercising, socializing and health monitoring within one life promoting environ.

The present invention includes a horseshoe-shaped table with computer and dual-purpose seat that adjusts to sizes sufficient to comfortably accommodate a user of various sizes and weights and which serves as both a chair and a seated weight scale that inputs the data on weight into the computer. Integrated within the table is a daily food scale where all of the dieter's food for the day is placed into and weighed with all data being fed into the computer. A smaller scale is also structured within the table that measures the weight of each individual meal and inputs the data into the computer to calculate the caloric content of that meal. A partitioned plate with removable segments is situated on the meal scale to allow for accurate measurement of different food groups by the computer. It can be removed and washed after use. The table has two personal external sensors. One is an elasticized band with an imbedded sensor which fits around the head and chin and over the mandible or jaw of the user and collects information on the amount of chewing or mastication and will be used to teach the user to slow the eating process. A pulse sensor is worn around the user's wrist and the data inputted therefrom will be used to mobilize the user into exercising before and after eating a meal. The data gathered by the various sensors and scales will permit the application of the cyber personal trainer to fulfill the functions of a real dietary councilor. The present invention will include several modes of support including on-line support that will alleviate social isolation by encouraging networking with similar people and allow inputted individual data to be collectively shared. People used to eating alone in shame and isolation could eat a cyber-regulated meal together. Instead of on-line chat rooms there could be on-line meal rooms. Another support mode will ensure training with privacy as the user utilizes the cyber personal trainer application off-line. This application will take inputted data on the user and structure a customized diet and exercise program for them while providing actual nutrition lessons.

2. Description of the Prior Art

Numerous diet control systems have been provided in prior art. Typical of these is U.S. Pat. No. 4,387,777 issued to Stephen R. Ash on Jun. 14, 1983.

Another patent was issued to Yianni Attikiouzel on Mar. 27, 1990 as U.S. Pat. No. 4,911,256. Yet another U.S. Pat. No. 4,924,389 was issued to Claude Gerbaulet et al. on May 8, 1990 and still yet another was issued on Aug. 13, 1993 to Mary J. Kretsch et al. as U.S. Pat. No. 5,233,520. Another patent was issued on May 2, 1995 to Gunes M. Ecer as U.S. Pat. No. 5,412,564.

Caloric counting method and apparatus comprises a base support structure, a plate support structure pivotally mounted on the base support structure, and scale means connected to said plate support structure at a point remote from the pivot line thereof. A plate carrying a combination of food components constituting an entire meal is positioned on the plate support structure to determine the total caloric content of the entire meal. The plate is provided with indicia defining different zones on the plate for foods having different calories per gram, these zones being arranged so that the zone corresponding to foods having the least calories per gram is positioned nearest the pivotal mounting of the plate support structure when the plate is positioned thereon. The patient places the food components constituting an entire meal in the correct zones on the plate and the total caloric content of the entire meal is determined in a single operation by reading the scale which is calibrated in calories.

A dietetic measurement apparatus having computer means having a controlling instruction means to provide a determination of basic integers for a mass of a food item weighed on a weighing means. The weighing means provides a weighing signal, in the form of a logical periodic signal, to a central processor unit of the computer means, which measures the frequency of the weighing signal and correlates the mass of the food item and the quantities of the nutrients. The nutrients comprise carbohydrate, calcium, cholesterol, fat, fiber, iron, protein, sodium and calorific content. Also a number of command keys are provided and include a ZERO key and a BOWL key to aid in weighing procedures.

A first memory stores a calorie goal and quantities of food in several categories which a person anticipates will be consumed during a predetermined day. The quantity of food eaten during the preceding days are stored in a second memory. A computer determines the recommended number of calories and quantities of food in each category for the predetermined day as a function of the quantities consumed during the preceding days. The recommended quantities are stored in a third memory and comparisons are made between the estimated quantities and the recommended quantities, the results of which are displayed. The device, used with or without scales, provides for a healthy and balanced nutrition.

An interactive computerized dietary measurement system and process which can be used by lay people for accurate measurement of the intake of foods, nutrients, and other food components in the diet. The system includes a computer device coupled with an electronic balance, output/display device(s), user input element(s), a food codes database and a storage element. The system has the ability to provide a plurality of weigh-in measurement options with respect to different food service settings or habits and to respectively tag the measurement of each of the options selected by the user in the storage element so as to track the measurements. The system can instruct user on the next measurement action and required input so that users are not required to remember all of the measurement actions and sequences of the actions for the measurements. The system also provides a plurality of weigh-out measurement options in which the computer will track the measurement record and remind the user of what has been done and what should be done so that a complete and accurate collection of dietary intake data can be achieved. The system is further capable of signaling to the user any weighing errors for allowing user to correct the errors, and of permitting user to make comments or notes as to measurements.

A system and a method for recording and monitoring of dietary consumption by a consumer is disclosed. The system consists of a computer for storing and processing nutritional information of the type used for diet control, a real time clock for maintaining current date record, a product code entry terminal or a bar code reader for inputting product identification information, a read-write unit adapted to receive one or more integrated circuit (IC) cards of the smart card type having memory and a microprocessor for reading and writing nutritional information into and from a smart card, a printer for printing nutritional information, and optionally an electric display for displaying such information. Consumer inserts his/her personalized smart card into card reader writer before a purchase transaction starts at a food store or a restaurant checkout counter. As foods and drinks are purchased, dietary nutritional consumption data is electronically collected, sorted, and combined with historical daily averages of nutritional consumption data stored in consumer's personalized smart card and daily averages of nutrition consumption along with other nutritional and personal data is printed out as a report to the consumer at the end of the purchase transaction. Nutritional data may include personal consumption data on calories, calories from fat, calories from sugars, and cholesterol, dietary fibers, sodium, carbohydrates, proteins, and the like. Consumer's smart card serves as a personal nutritional consumption history file, and is updated each time it is used.

While these diet control systems may be suitable for the purposes for which they were designed, they would not be as suitable for the purposes of the present invention, as hereinafter described.

SUMMARY OF THE PRESENT INVENTION

The present invention discloses a horseshoe-shaped table having a computer and a dual-purpose chair associated therewith. The chair adjusts to variously sized users by using a piston and piston support mechanism disposed internally of the chair. The chair also serves as a weight scale or sensor which is disposed in the seat thereof and has data input means, including a headset with microphone and chewing sensor disposed thereon. The arm of the chair has a blood pressure and pulse sensor disposed thereon. Data gathered from the sensor input devices is transmitted to a computer disposed internally of the table having a monitor and keypad disposed on the tabletop. Also shown are a pair of scales which measure both the individual meal food and the daily food allowance which data is also input into the computer. The scales are equipped with segmented platters and non-segmented platters, having various food compartments for receiving different types of food. The monitor is disposed on a suspension arm which is adjustable and is provided with a control crank for adjusting the arm. The data inputs are disposed near the computer in order to receive input data from the input devices. An alternative embodiment of the present invention is disclosed wherein data is transmitted from the chair via electromagnetic wave means to the table wherein the chair is electrically operated and the monitor, and food scales are mounted internal of the table being covered by panels in the closed position and having a control panel for electrically raising these elements from internal of the tables.

A primary object of the present invention is to provide interactive furniture for dieter's that will promote behavior modification, socialization, and knowledge for obese people.

An additional object of the present invention is to provide interactive furniture for dieter's including a table with a computer and two scales and an expandable seat with a plurality of sensors to monitor the user's weight, vital signs, and mastication rate and input the gathered data into the computer.

A further object of the present invention is to provide interactive furniture for dieter's wherein the table scales are used to measure the weight of one days food and the weight and caloric content of each individual meal with the data from each scale then inputted into the computer.

A yet further object of the present invention is to provide interactive furniture for dieter's wherein the computer uses all the inputted in data from the chair sensors, the scales and exercise equipment to determine a diet and exercise regimen appropriate for that individual thereby acting as a personal trainer.

Another object of the present invention is to provide interactive furniture for dieters wherein the computer allows the user to go on-line to form support groups and exchange data with other users of the present invention.

Another object of the present invention is to provide interactive furniture for dieters that is economical in cost to manufacture.

Another object of the present invention is to provide interactive furniture having a pulse sensor thereon which will be used to encourage the user to increase the pulse rate by activity or exercise before sitting down to eat.

Another object of the present invention is to provide interactive furniture wherein exercise equipment is integrated with the computer as well in order to accept inputed data including distance, coloric content, etc.

Further objects of the present invention will appear as the description proceeds.

To the accomplishments of the above and related objects, this invention may be embodied in the form illustrated in the accompanying drawings, attention being called to the fact, however, that the drawings are illustrative only, and that changes may be made in the specific construction illustrated and described in the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

LIST OF REFERENCE NUMERALS

Figure 1:
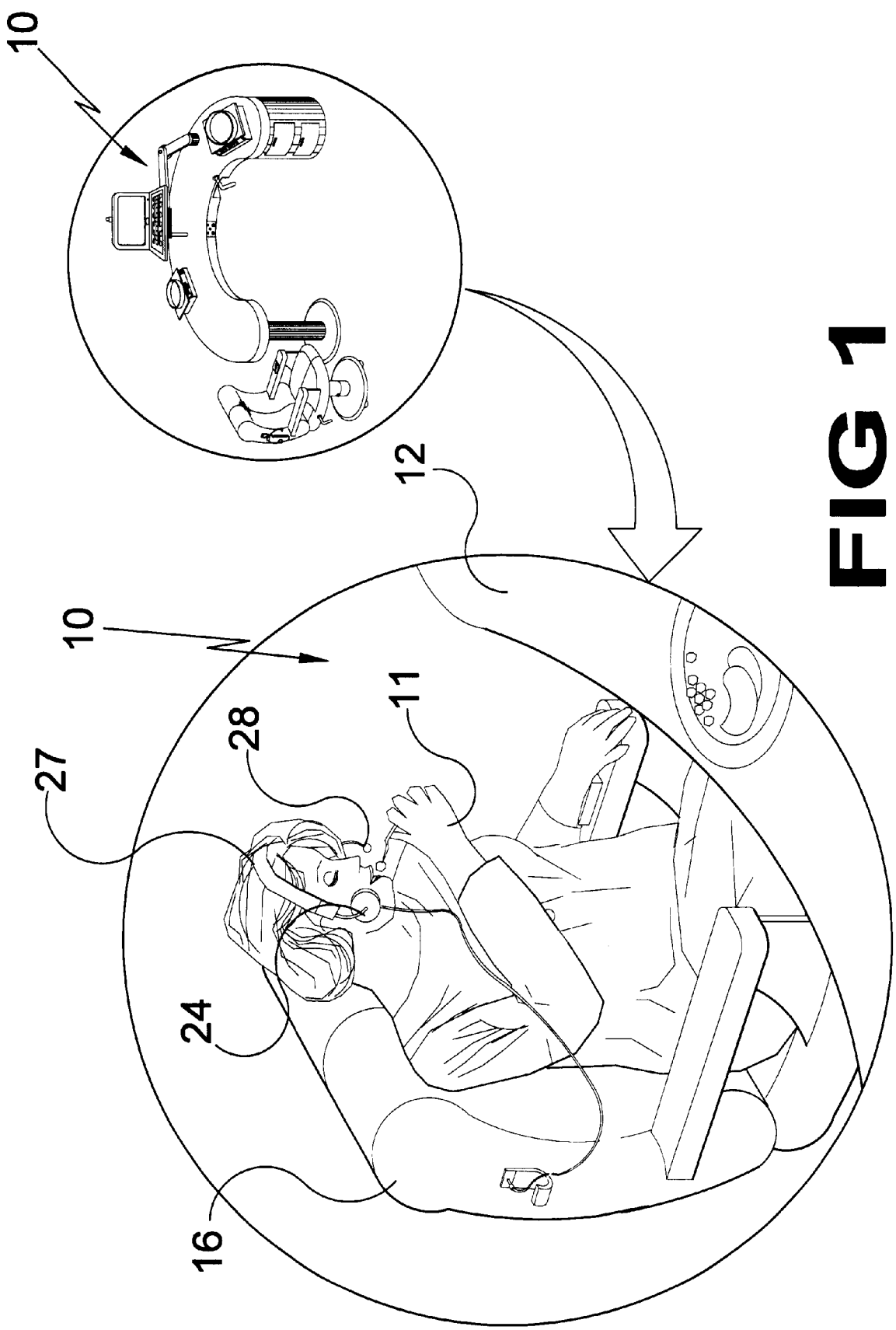
FIG. 1 is a perspective view of the present invention in use.

With regard to reference numerals used, the following numbering is used throughout the drawings.
10 present invention
11 user
12 table
14 computer
16 chair
18 weight sensor
20 daily food scale
22 individual meal scale
24 chewing sensor
26 blood pressure sensor
27 head set
28 microphone
30 chair adjustment arm
32 caster
34 chair base
36 chair arm
38 jack for blood pressure sensor and pulse sensor
40 monitor
42 key pad
44 monitor control handle
46 auxiliary ports
48 input for blood pressure sensor and pulse sensor
50 LCD display
52 input for microphone/chewing sensor
54 computer access drawers
56 rear access panel
58 suspension arm
60 crank for arm
62 recess of table
64 camera
66 segments of arm
68 pivot means
70 arm gear box
72 wiring harness
74 power distribution unit
76 line to power supply
78 pistons
80 piston support
82 stretch material
84 input jack
86 coil wire
88 storage hook
90 segmented platter
92 food compartment
94 food compartment
96 food compartment
98 food compartment
100 food compartment
102 food compartment
104 non-segmented platter
106 wiring harness
108 exercise bike
110 treadmill
111 data receiver
112 panel
114 control panel
116 data transmitter

DESCRIPTION OF THE PREFERRED EMBODIMENT(S)

In order that the invention may be more fully understood, it will now be described, by way of example, with reference to the accompanying drawings in which FIGS. 1 through 14 illustrate the present invention being interactive furniture for dieters.

Turning to FIG. 1, shown therein is a perspective view of the present invention 10 in use. Shown is a user 11 positioned in the chair 16 at the table 12 wearing the headband 27 with chewing sensor 24 and microphone 28 attached thereto.

Figure 2:
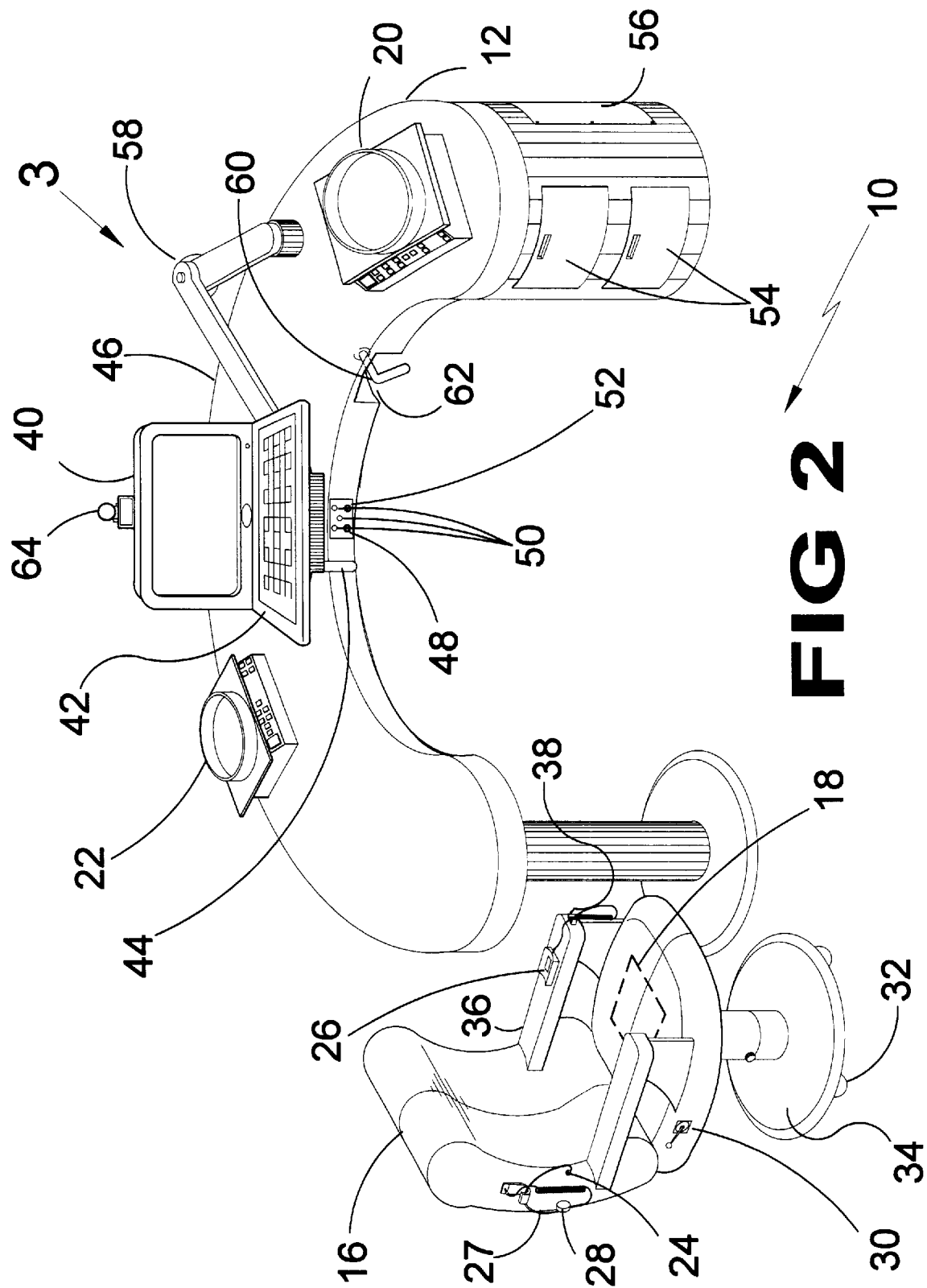
FIG. 2 is a perspective view of present invention.

Turning to FIG. 2, shown therein is a perspective view of present invention 10. The present invention 10 includes a table 12 with a computer (not shown but see FIG. 5, Item 14) and dual-purpose, expandable manual seat or chair 16 that adjusts to sizes sufficient to comfortably accommodate a user of various sizes and weights and which serves as both a chair 16 and a seated weight scale or sensor 18 that inputs the data on weight into a computer. The table 12 can be made in numerous shapes and sizes. Integrated within the table 12 is a daily food scale 20 where all of the dieter's food for the day is placed onto and weighed with all data being fed into the computer. A smaller, second scale 22 is also situated on the table 12 that measures the weight of each individual meal and inputs the data into the computer to calculate the caloric content of that meal. A partitioned plate (not shown) with removable segments is situated on the meal scale 22 to allow for accurate measurement of different food groups by the computer. It can be removed and washed after use. The table has two personal external sensors. One is an elasticized band 27 with an imbedded sensor 24 which fits around the head and chin and over the mandible or jaw of the user and collects information on the amount of chewing or mastication and will be used to teach the user to slow the eating process. A sensor for blood pressure and pulse 26 is worn around the user's wrist or arm and the data inputted therefrom will be used to mobilize the user into exercising before and after eating a meal. The data gathered by the various sensors and scales will permit the application of the cyber personal trainer to fulfill the functions of a real dietary counselor. Also shown associated with the chair 16 is the manual control adjustment knob 30 along with a plurality of casters 32 disposed on the underside of the chair base 34 showing the blood pressure sensor 26 attached to the arm 36 of the chair along with a blood pressure sensor jack 38. Shown are the monitor 40 along with a keypad 42 and a manual monitor control handle 44. Also shown are auxiliary ports 46, a blood pressure and pulse sensor input 48, an LCD display 50 for the display of chewing sensor data, blood pressure and weight input data. Also shown is a microphone/chewing sensor input 52 which would allow the user to be online and enter data/text without having to utilize the keyboard while eating. Note that table inputs 46, 48 and 52 are situated on the table but they may also have corresponding input means disposed on the chair. Shown associated with the table 12 are computer access drawers 54 containing the computer along with a rear access panel 56. Also shown is a suspension arm 58 for movably adjusting the monitor 40 along with a manual suspension arm control crank 60 which is disposed in a recessed area 62 of the table 12. Also shown is a camera 64 for use with the computer.

Figure 3:
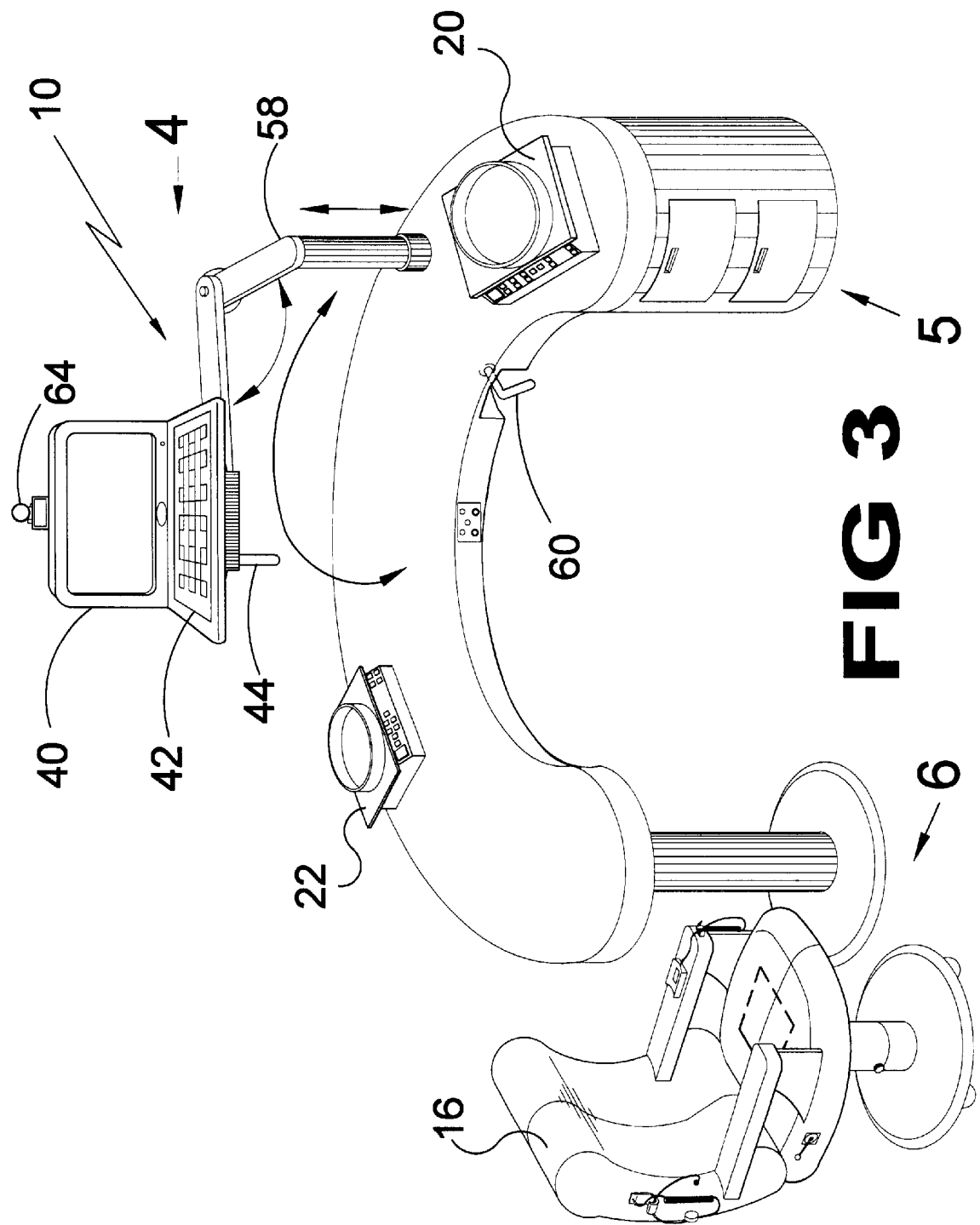
FIG. 3 is a perspective view of the present invention showing the movement of the computer monitor on the suspension arm.

Turning to FIG. 3, shown therein is a perspective view of the present invention 10 showing the manually controlled movement of the computer monitor 40 on the suspension arm 58. Other elements previously disclosed are also shown.

Figure 4:
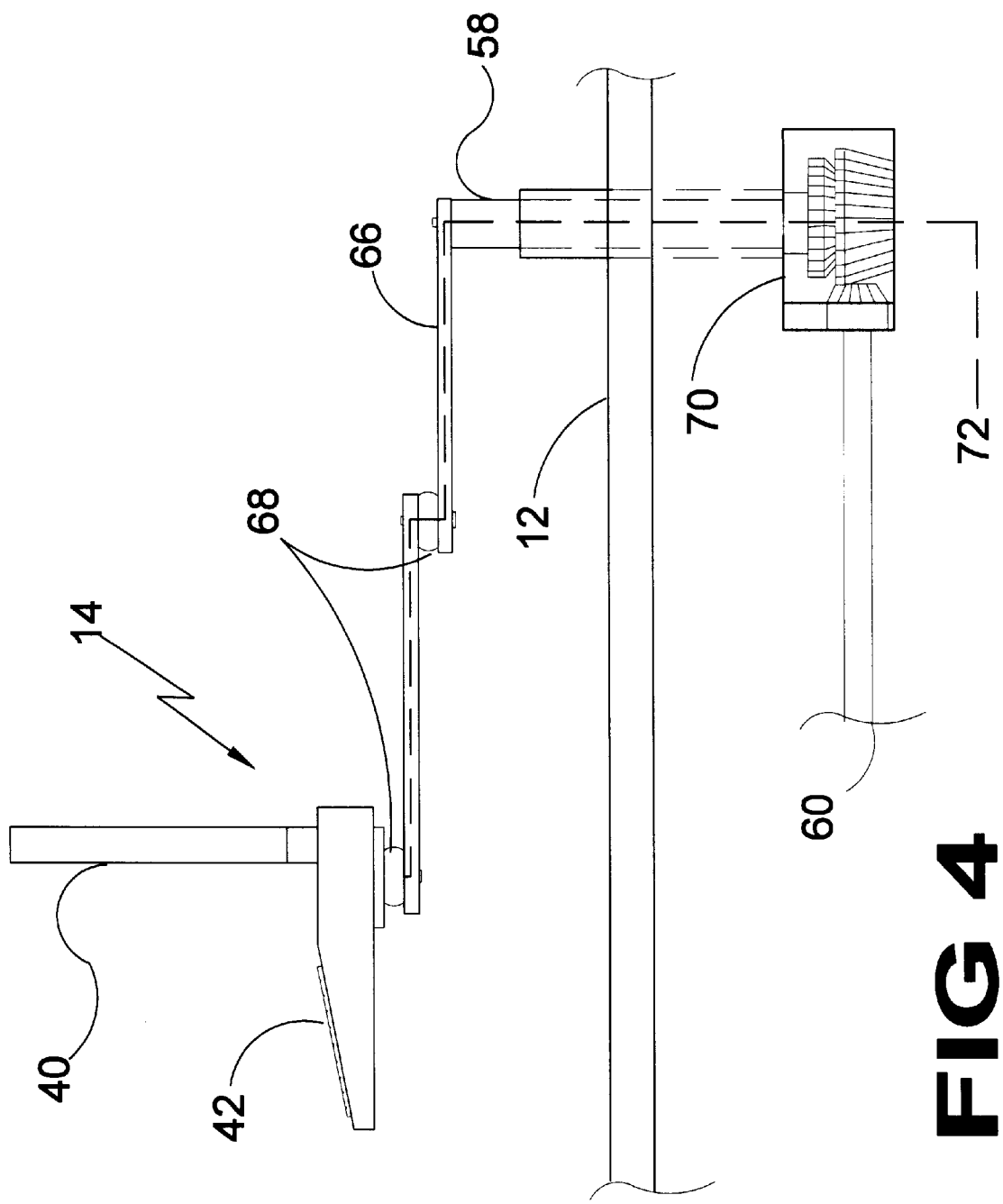
FIG. 4 is side view of the suspension arm mechanism.

Turning to FIG. 4, shown therein is side view of the suspension arm mechanism 58. Shown is an extension arm 60 which is an extension of the manual suspension arm crank handle along with segment members 66 of the extension arm 58 connected by pivotal means 68 showing the computer monitor 40 mounted on the end member thereof. Also shown is a gear box 70 along with a wiring harness 72 which travels internally through the hollow extension arm to the computer 14.

Figure 5:
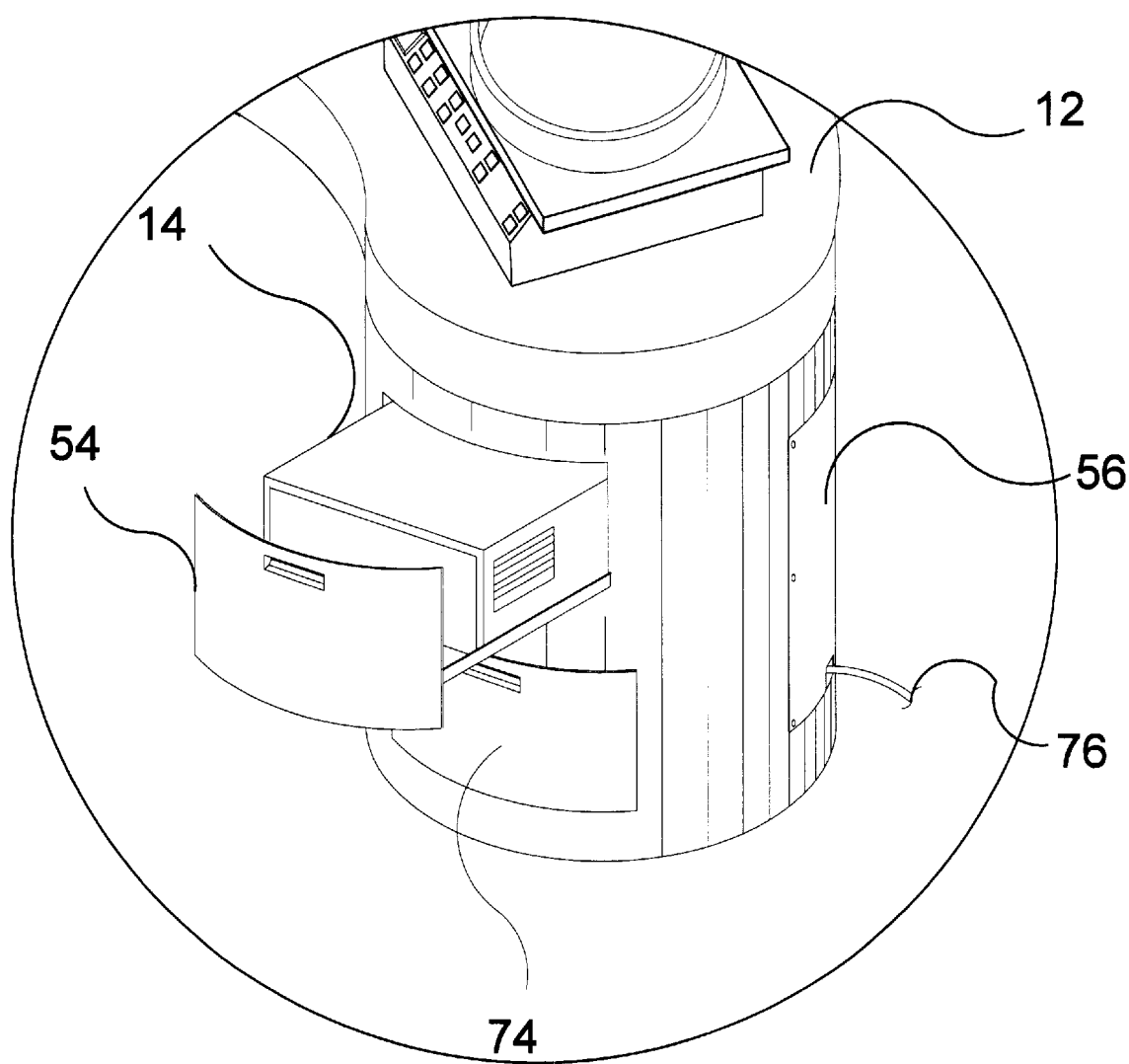
FIG. 5 is a perspective view of the computer and power supply housing portions of the table.

Turning to FIG. 5, shown therein is a perspective view of the computer 14 and power supply distribution unit 74 housed in an interior portion of the table 12 along with line 76 to the power supply. Note that all wires and cables associated with the present invention are housed internal of the table 12 so as to make the present invention more esthetically appealing. Other elements previously disclosed are also shown.

Figure 6:
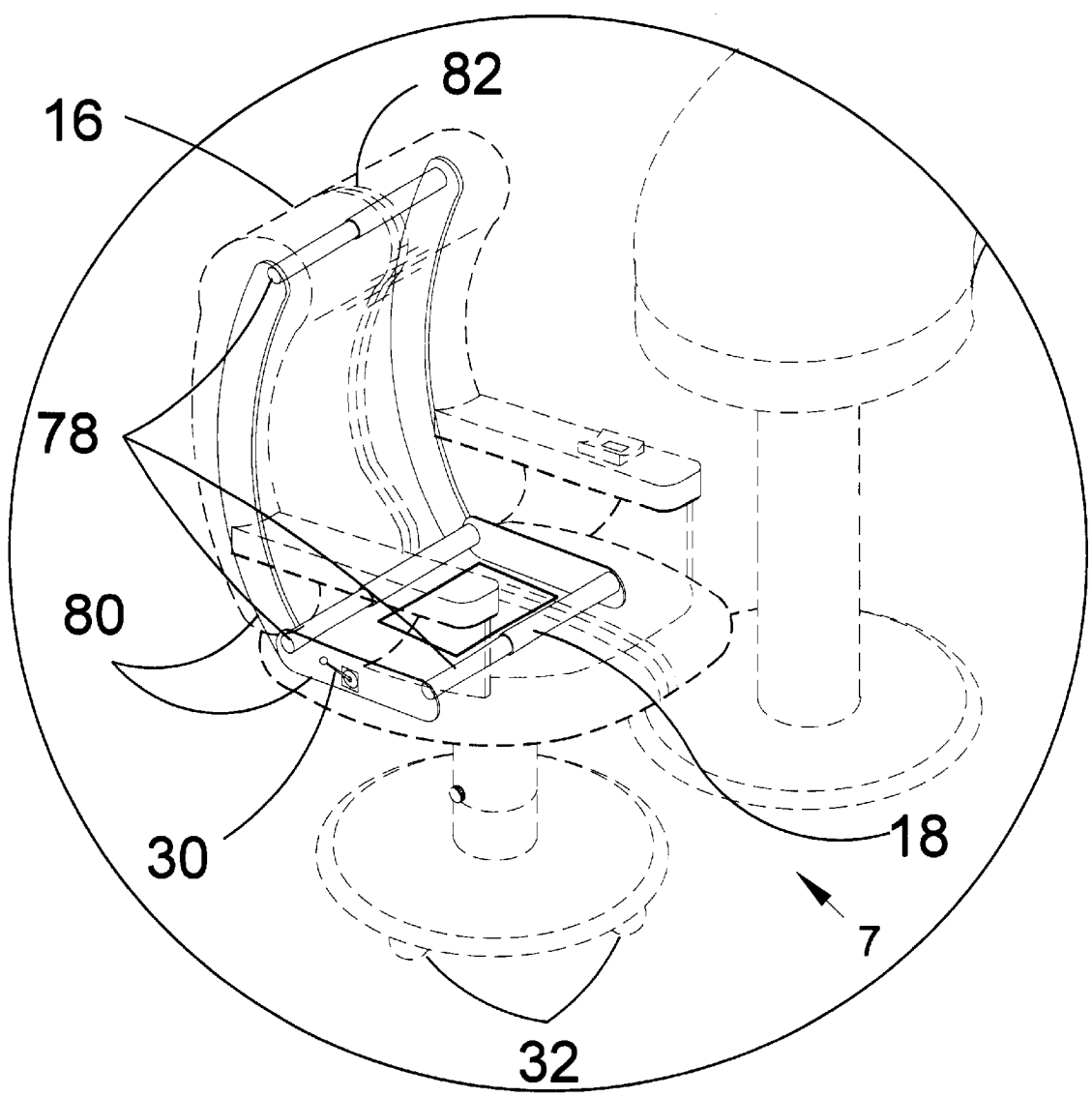
FIG. 6 is a perspective view of the chair expansion mechanism.

Turning to FIG. 6, shown therein is a perspective view of the chair 16 expansion mechanism. Shown are a pair of expandable pistons 78 which are internally disposed within the chair 16 which are hydraulically or like operated which can expand the chair 16 and which also utilizes lateral piston supports 80 to provide a support frame for the pistons 78. Stretch material 82 used on the external surface of the chair is also shown. Other elements previously disclosed are also shown.

Figure 7:
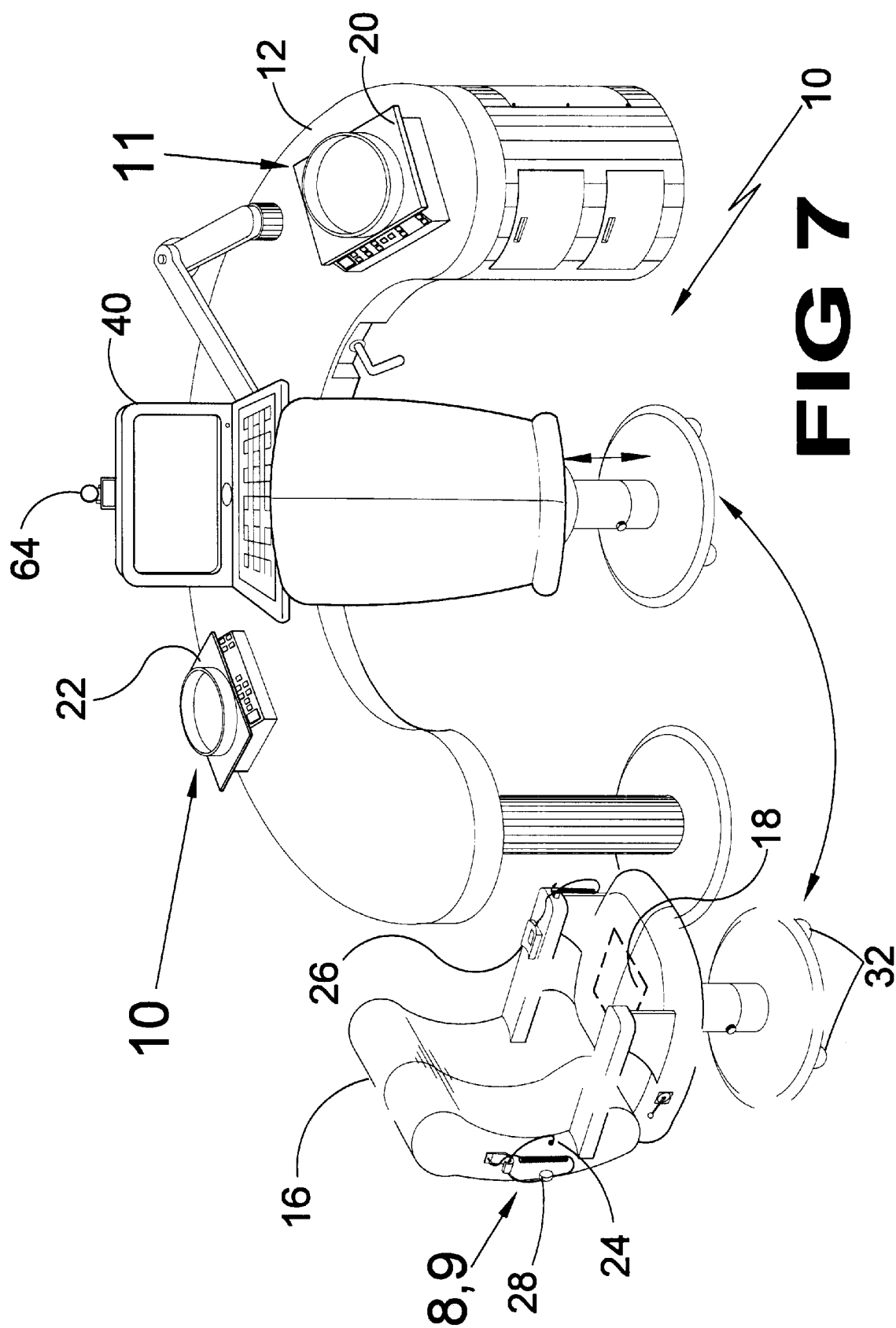
FIG. 7 is a perspective view of the present invention.

Turning to FIG. 7, shown therein is a perspective view of the present invention 10. Other elements previously disclosed are also shown.

Figure 8:
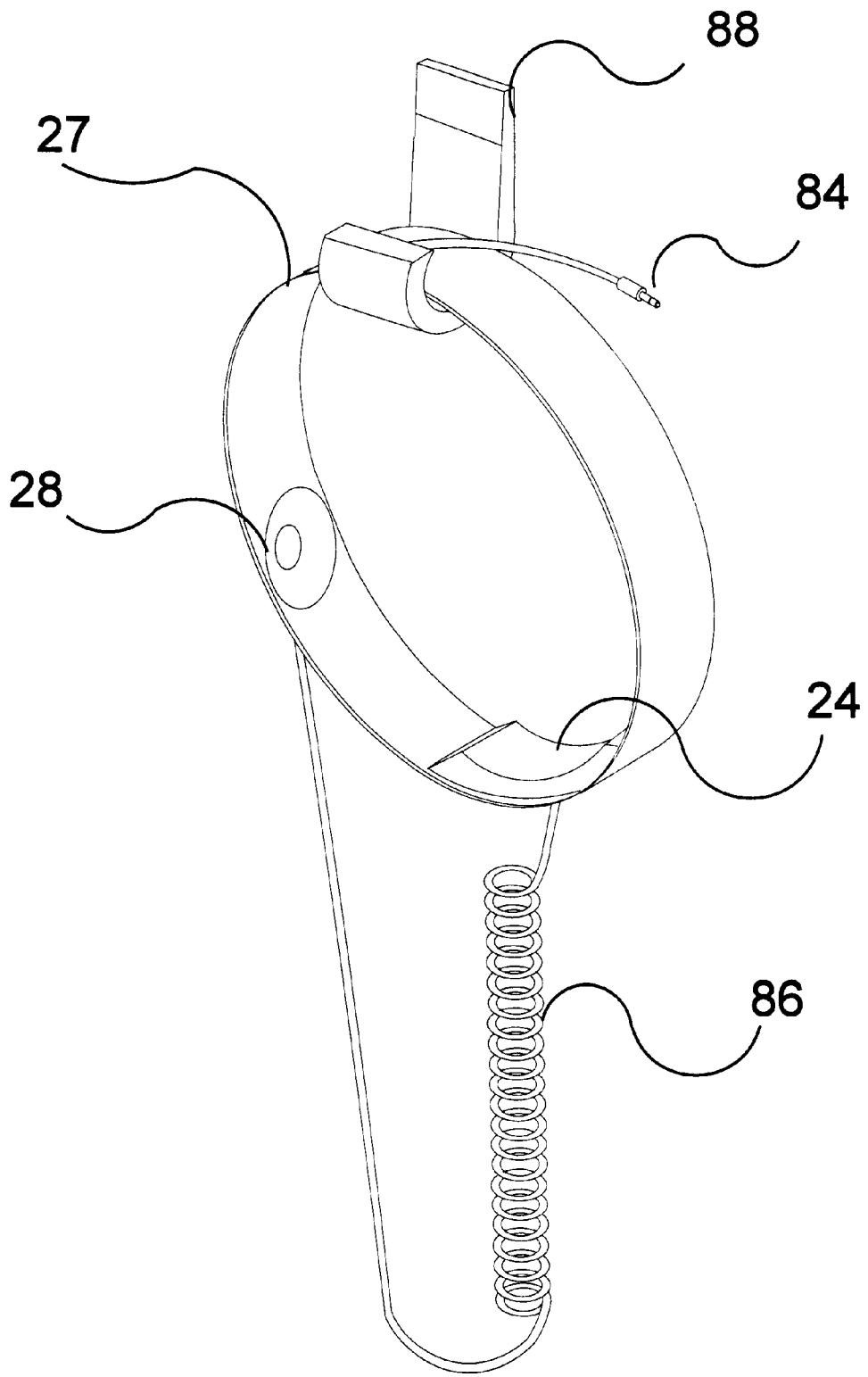
FIG. 8 is a perspective view of the headset with chewing sensor and microphone.

Turning to FIG. 8, shown therein is a perspective view of the elastic or fabric headset or head band 27 with chewing sensor 24 and microphone 28. Also shown is an input jack 84, coiled microphone/chewing sensor wire 86 and head set storage hook 88.

Figure 9:
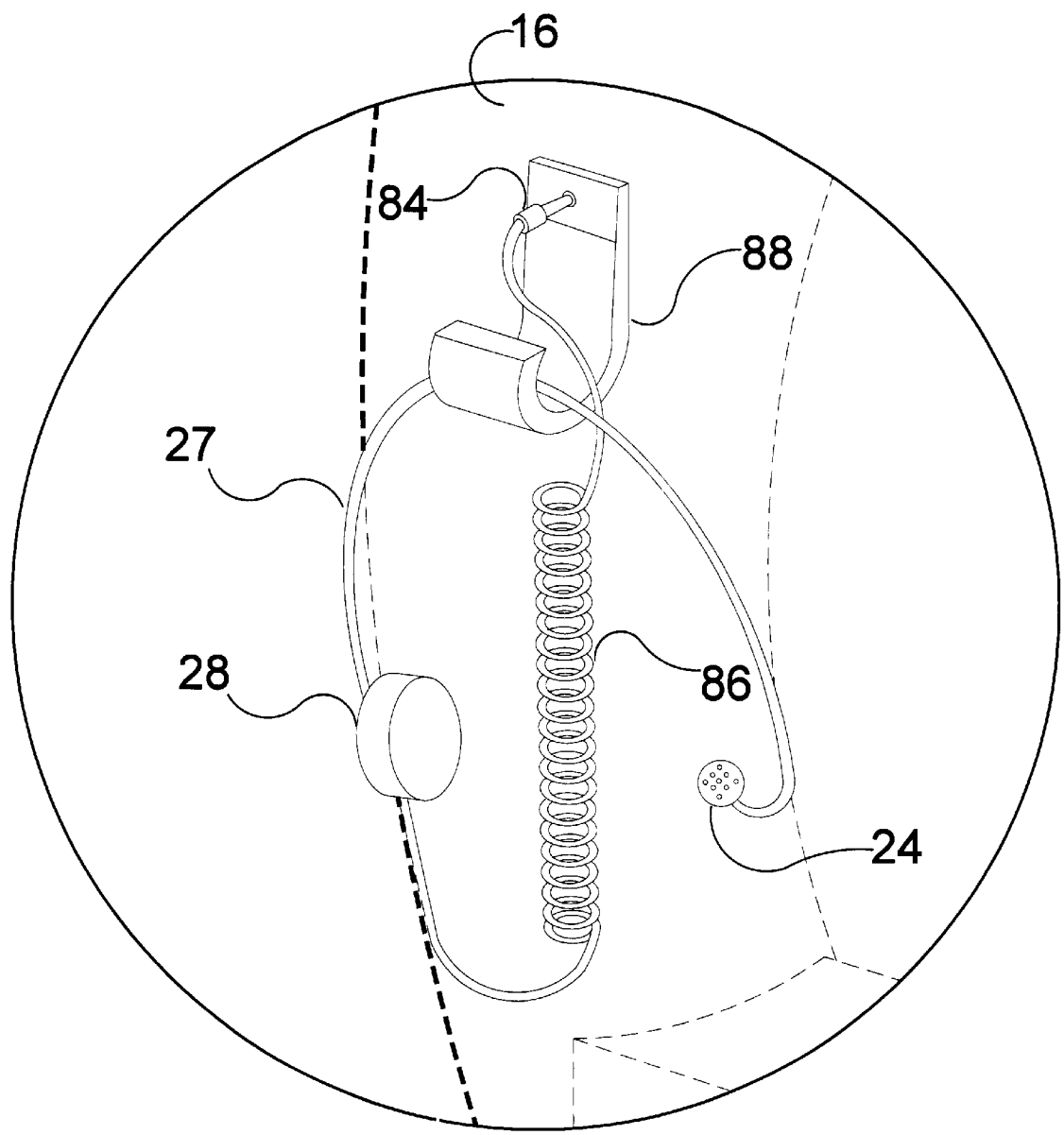
FIG. 9 is a perspective view of the headset with chewing sensor and microphone.

Turning to FIG. 9, shown therein is a perspective view of an alternative headset 27 with chewing sensor 24 and microphone 28. The input jack 84 is shown disposed in a mating male jack in the side of chair 16. Other elements previously disclosed are also shown.

Figure 10:
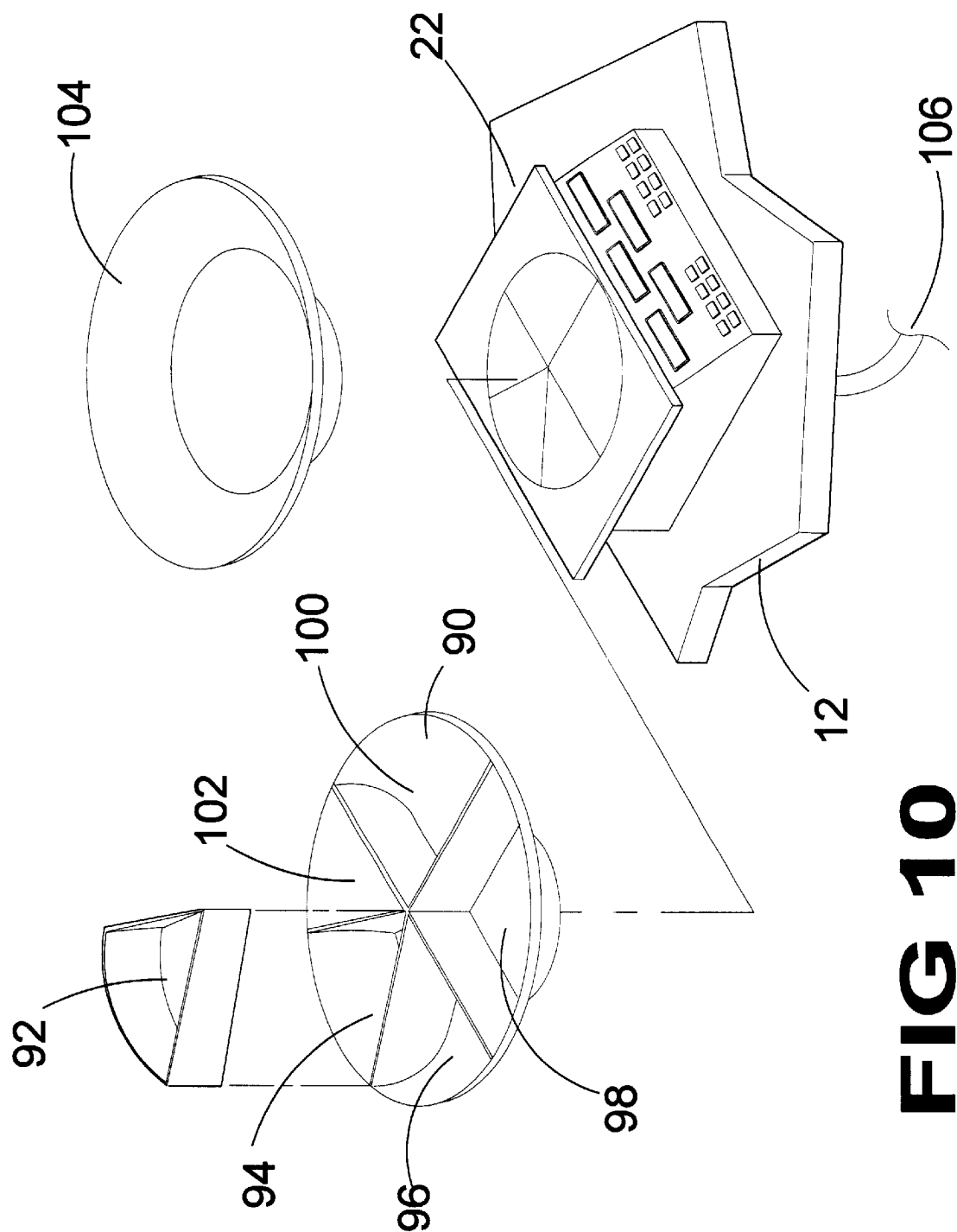
FIG. 10 is a perspective view of the individual meal scale and segmented platter.

Turning to FIG. 10, shown therein is a perspective view of the individual meal scale 22 and segmented platter 90. Shown is a removable, measuring food compartment 92 having multiple sections for example, for breads and cereals 94, milk and cheese 96, vegetables and fruit 98, meats, fish, poultry and beans 100, and fats, sweets and alcohol 102. Also shown is a non-segmented platter 104. Also shown is the internal wiring harness 106 which connects to the power source. Other elements previously disclosed are also shown.

Figure 11:
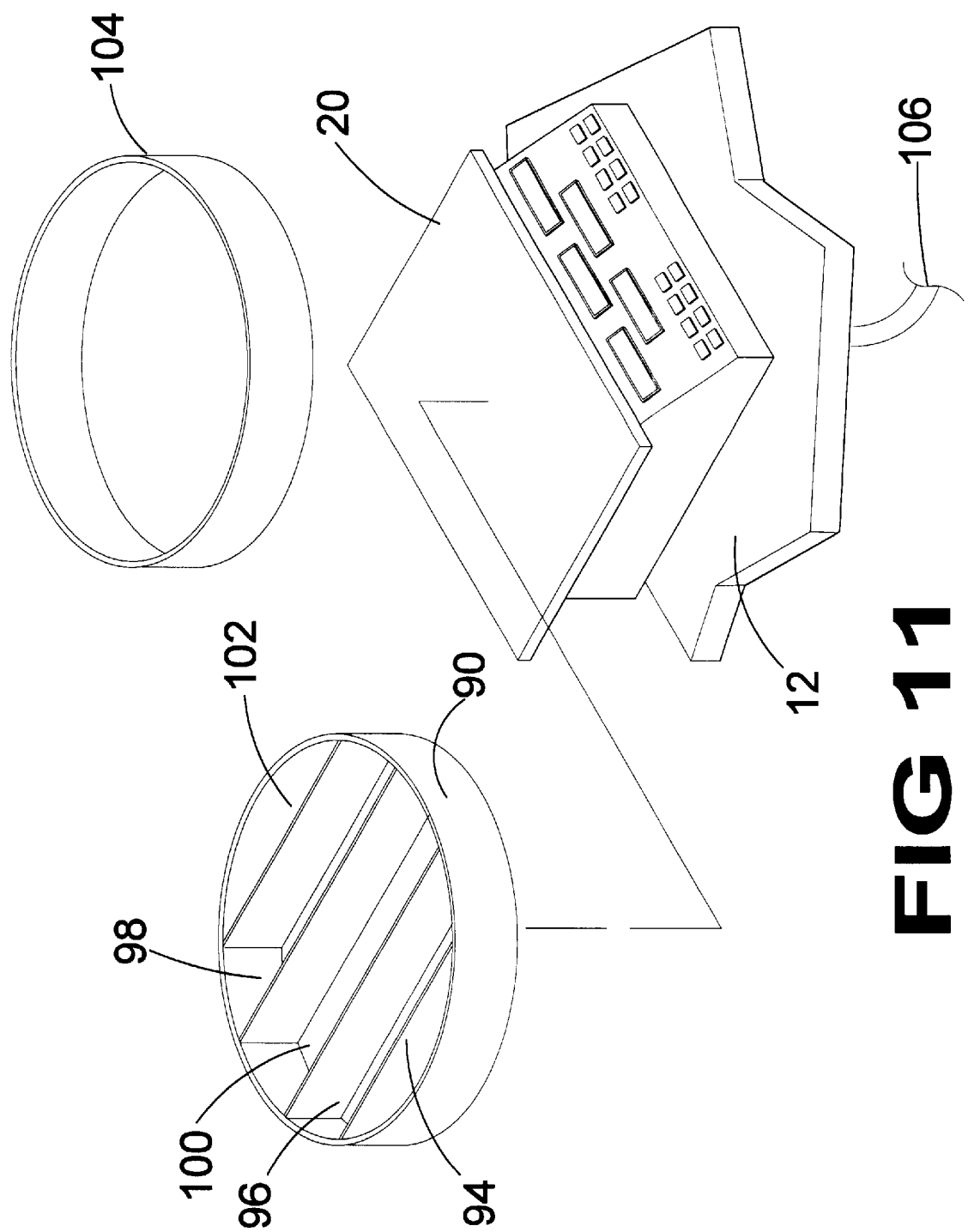
FIG. 11 is a perspective view of the daily total meal scale and platters.

Turning to FIG. 11, shown therein is a perspective view of the daily total meal scale 20 and platters 90 thru 104. Other elements previously disclosed are also shown.

Figure 12:
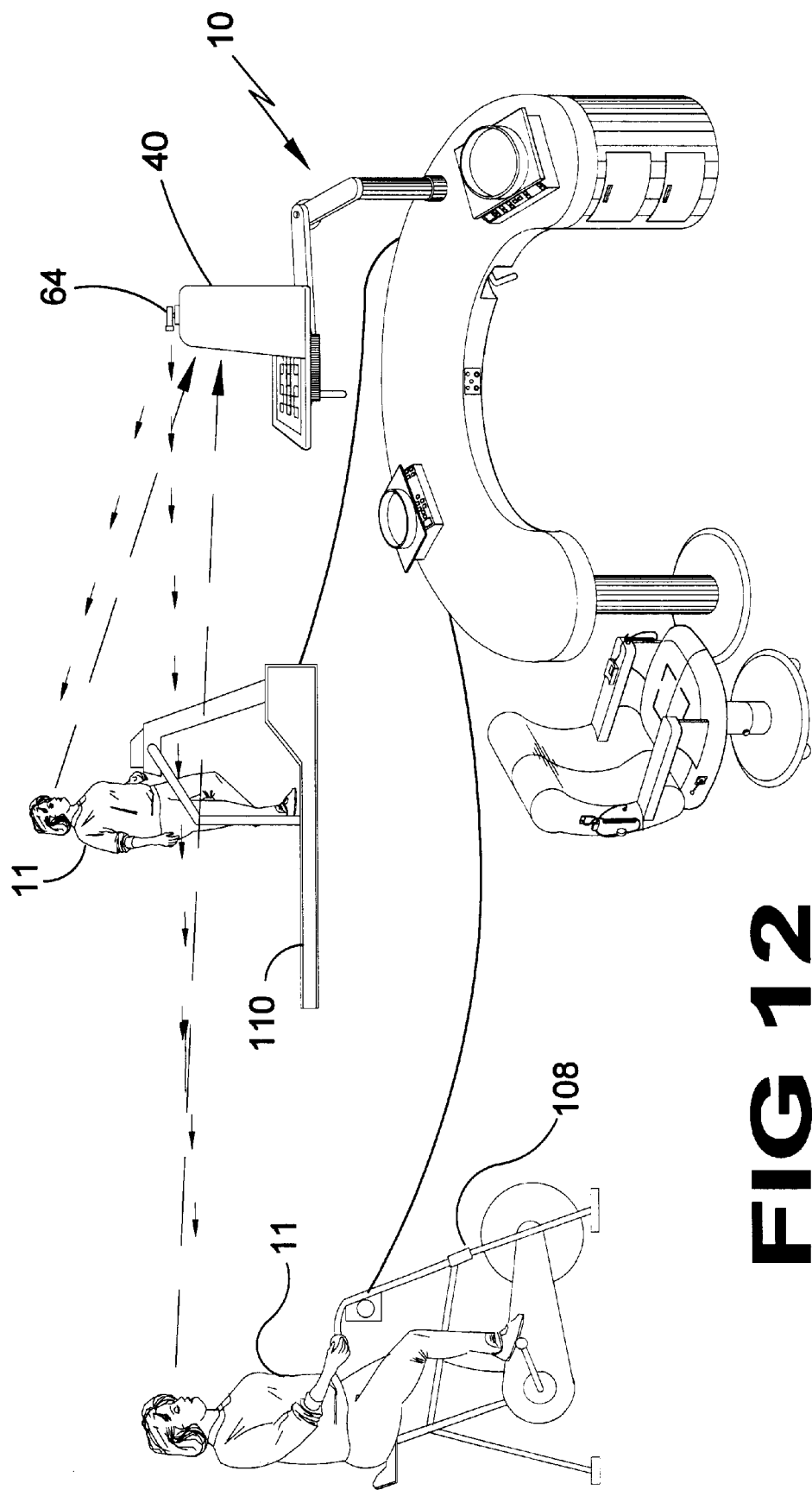
FIG. 12 is a side view of the present invention demonstrating how various types of exercise equipment could be inputted into the computer while the user works out with her on-line support group via the camera and the monitor.

Turning to FIG. 12, shown therein is a side view of the present invention 10 demonstrating how various types of exercise equipment could be inputted into the computer while the user works out with her on-line support group via the camera 64 and the monitor 40. Shown is a user 11 on an exercise bike 108 and a treadmill 110 interacting with a camera 64 and monitor 40.

Figure 13:
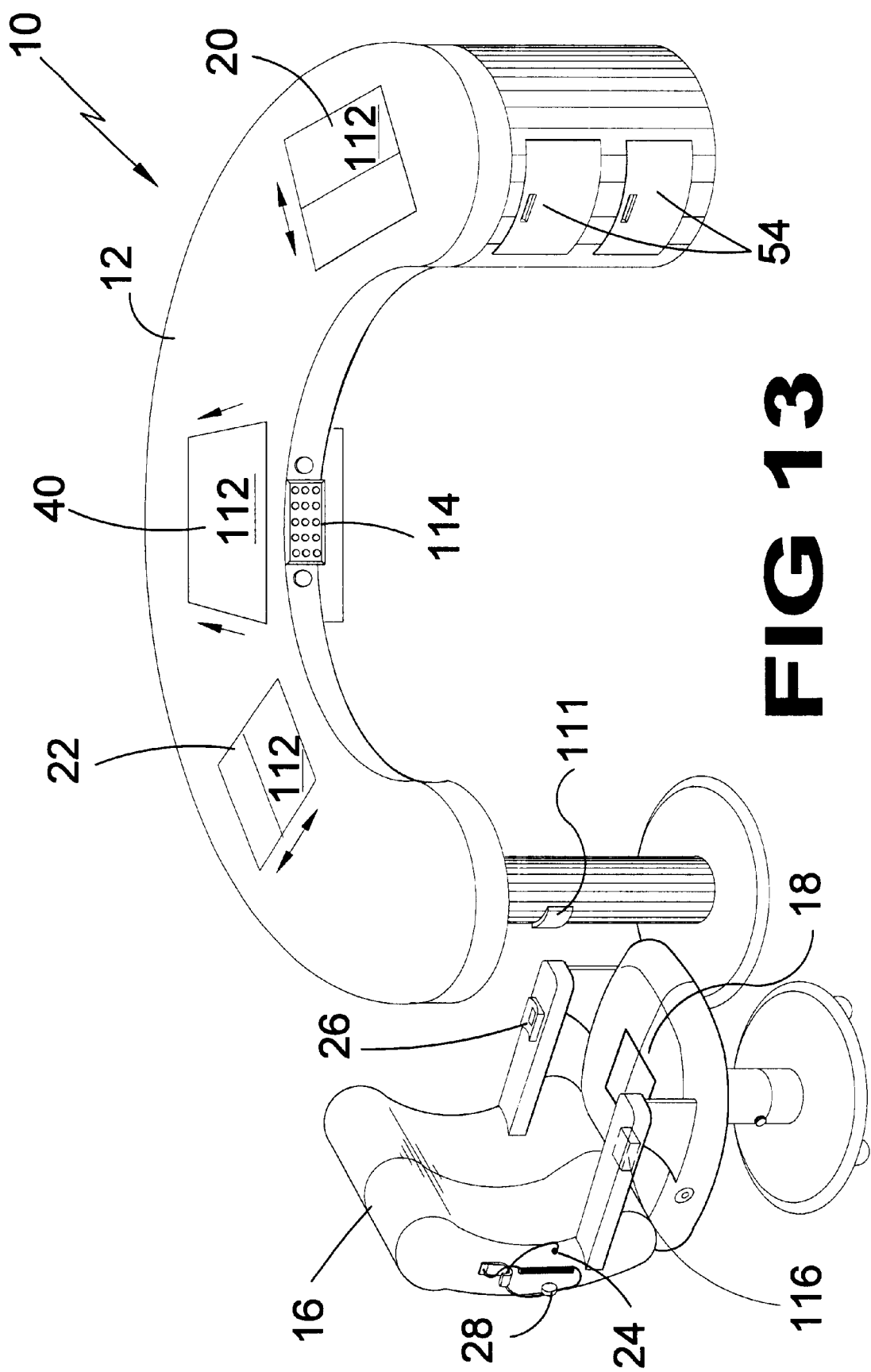
FIG. 13 is perspective view showing an alternate embodiment of the present invention wherein data is transmitted from the chair to the table and the monitor and scales are recessed within the table and are uncovered as needed.

Turning to FIG. 13, shown therein is perspective view showing an alternate embodiment of the present invention 10 wherein the chair 16 expands electronically and data is transmitted and received by electromagnetic means 111, 116 as would be done by one skilled in the art being, e.g., RF, infrared or like means, to the table 12 and the monitor 40 and scales 20, 22 are recessed and concealed under panels 112 within the table 12 and are uncovered as needed. Also shown are a monitor control panel 114 and other elements previously disclosed.

Figure 14:
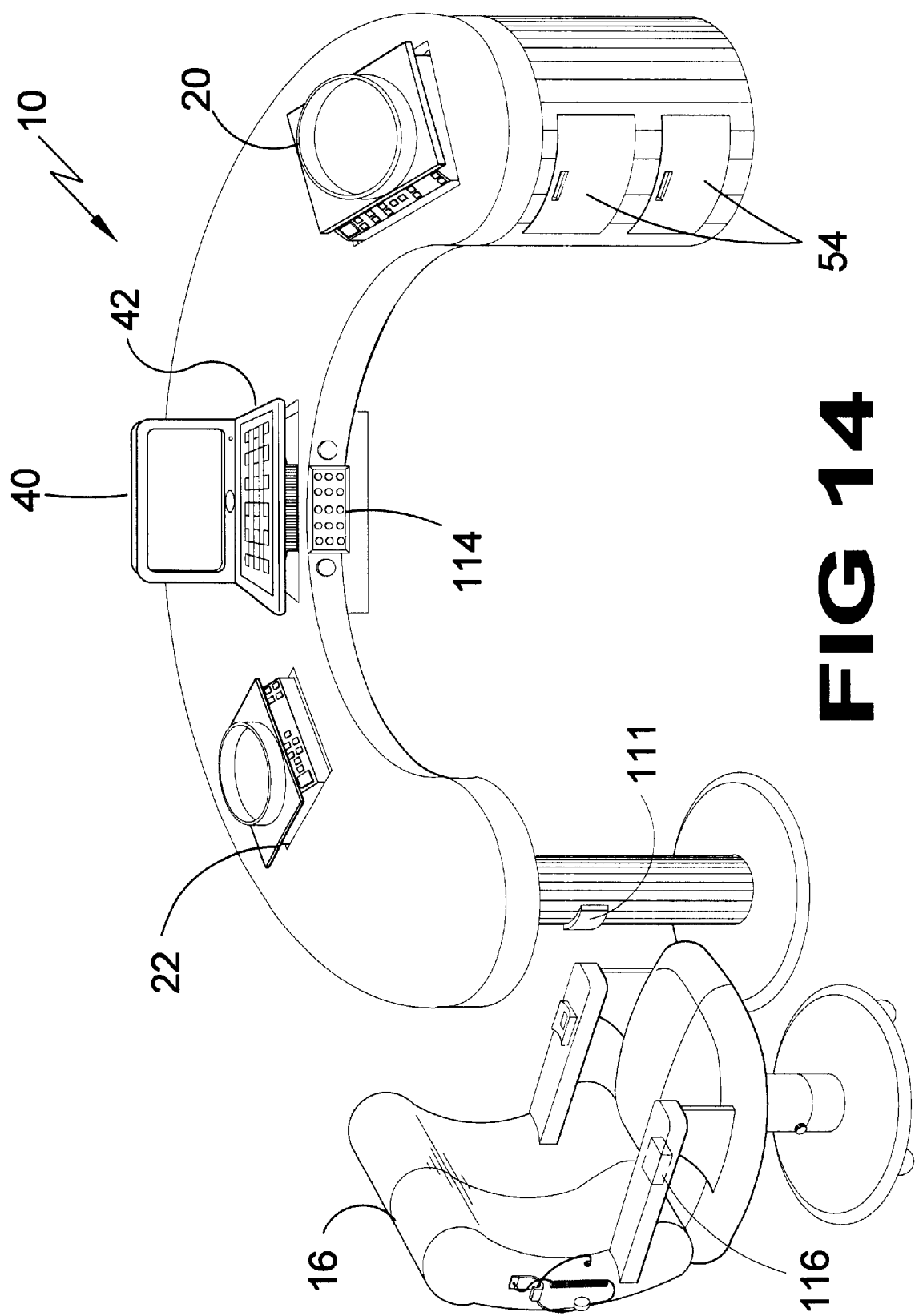
FIG. 14 is perspective view showing an alternate embodiment of the present invention.

Turning to FIG. 14, shown therein is perspective view showing an alternate embodiment of the present invention 10 showing the monitor 40, keypad 42, and scales 20, 22 having been opened by operating buttons on the control panel 114. Other elements previously disclosed are also shown.

What is claimed to be new and desired to be protected by Letters Patent is set forth in the appended claims.

I claim:

1. An apparatus for interactive furniture group for use by a dieter, comprising:

a) a table for placement thereupon of various items used with the apparatus;

b) at least one scale for weighing food portions of the dieter;

c) a chair for use by the dieter, said chair being moveable d) means for a plurality of sensors disposed on said chair, said sensors for gathering data about the dieter;

e) a computer disposed on said table, said computer having a monitor and a keyboard, said computer for receiving and processing data from said means for a plurality of sensors and from said scale;

f) said table is U-shaped for placement of said chair therein said U-shape;

g) said table further comprises a lower access drawer internal thereof, said drawer disposed proximate to said chair, said access drawer for receiving said computer, said table further comprising a rear access panel;

h) said monitor and said keyboard are disposed on top of said table, further comprising a wiring harness for connection to said computer;

i) a movable suspension arm disposed on said table for receiving said monitor and said keyboard;

j) said suspension arm further comprises a plurality of sections, said sections being pivotally joined, said sections being hollow for receiving said wiring harness for joining said computer to said monitor and said keyboard;

k) said suspension arm further comprises means for a gear box whereby said arm is movably adjustable, wherein said means for a gear box further comprises a control handle, said control handle being disposed on said table;

l) said scale further comprises a segmented platter having a plurality of removable food compartments therein, said food compartments for receiving different categories of food for consumption by the dieter; and m) said means for a plurality of sensors further comprises a weight sensor, a chewing sensor, a blood pressure sensor, a pulse sensor, and a microphone for gathering data from the dieter.

2. The apparatus of claim 1, wherein said scale consists of two scales, being a first scale for weighing individual meals and a second scale for weighing the total daily food consumption.

3. The apparatus of claim 2, wherein said chair further comprises means for expansion disposed internal said chair whereby the size of said chair can be varied to receive various sizes of dieters.

4. The apparatus of claim 3, wherein said means for expansion further comprises a plurality of expandable pistons and lateral piston supports, said pistons being hydraulically operated so as to vary the size of said chair.

5. The apparatus of claim 4, wherein said chair is mounted on a base, said base having a plurality of casters disposed thereon to provide movability to said chair.

6. The apparatus of claim 5, wherein said weight sensor is disposed internal of the seat of the chair to record data about the weight of the dieter.

7. The apparatus of claim 6, further comprising a headset, said headset for receiving said chewing sensor and said microphone, said chewing sensor adapted to be disposed contiguous to the jaw of the dieter.

8. The apparatus of claim 7, wherein said blood pressure sensor and said pulse sensor are disposed on an arm of said chair proximate to the dieter.

9. The apparatus of claim 8, further comprising a plurality of computer input jacks disposed on said table, said jacks receiving connection means from said means for a plurality of sensors for transmission of data to said computer.

10. The apparatus of claim 9, further comprising means for concealing said monitor, said keyboard and said pair of scales internal said table, further comprising a panel for covering said means for concealing so that said panel is flush with the top of said table.

11. The apparatus of claim 10, further comprising an electrical control panel disposed on said table for controlling the operation of said means for concealing said monitor, said keyboard, and said first and second scale.

12. The apparatus of claim 11, further comprising means for transmitting data from said chair to said table, whereby data is transmitted by electromagnetic waves from the chair to the table.

* * * * *